United States Patent [19]

Driscoll et al.

[11] Patent Number: 4,788,181
[45] Date of Patent: Nov. 29, 1988

[54] 5-SUBSTITUTED-2',3'-DIDEOXYCYTIDINE COMPOUNDS WITH ANTI-HTLV-III ACTIVITY

[75] Inventors: John S. Driscoll, Rockville; Victor E. Marquez, Gaithersburg; Chong-Ho Kim, Hyattsville; James A. Kelley, Silver Spring, all of Md.

[73] Assignee: The United States of America as represented by the Department of Health and Human Services, Washington, D.C.

[21] Appl. No.: 913,575

[22] Filed: Sep. 29, 1986

[51] Int. Cl.[4] .................... A61K 31/70; C07H 19/06; C07H 19/10
[52] U.S. Cl. ........................................ 514/49; 536/23; 536/29
[58] Field of Search ............... 536/23, 29, 27; 514/48, 514/49

[56] References Cited

U.S. PATENT DOCUMENTS

| 3,346,562 | 10/1967 | Honjo et al. | 536/27 |
| 3,433,783 | 3/1969 | Honja et al. | 536/27 |
| 3,817,982 | 6/1974 | Verheyden et al. | 536/23 |
| 3,891,623 | 6/1975 | Vorbruggen et al. | 536/23 |

OTHER PUBLICATIONS

Sigma Chemical Company Catalog, Feb. 1984.

*Primary Examiner*—Johnnie R. Brown
*Assistant Examiner*—Jenny Tou
*Attorney, Agent, or Firm*—Browdy and Neimark

[57] ABSTRACT 5-substituted 2',3'-dideoxycytidine compounds and their monophosphates are disclosed which have been found to have potent activity against retroviruses. The 5-fluoro-and 5-aza-substituted 2',3'-dideoycytidine compounds have been found to be effective against HTLV-III/LAV virus.

8 Claims, No Drawings

5-SUBSTITUTED-2',3'-DIDEOXYCYTIDINE COMPOUNDS WITH ANTI-HTLV-III ACTIVITY

FIELD OF THE INVENTION

The present invention relates to novel 5-substituted-2',3'-dideoxycytidine compounds. These compounds, as well as their phosphorylated derivatives, have been found to have useful anti-retrovirus activity.

BACKGROUND OF THE INVENTION

Human T-lymphotropic virus type III (HTLV-III)/lymphadenopathy-associated virus (LAV) is a newly discovered retrovirus that is cytopathic for helper/inducer T cells in vitro. The virus is the etiologic agent of the acquired immune deficiency syndrome (AIDS) and related diseases. To date, thousands of cases of AIDS have been reported in the United States alone, and the incidence and prevalence of this disease continue to increase. AIDS is almost always fatal within 1 to 2 years after the first clinical manifestations of illness. This disease was initially described and characterized in four high-risk groups (homosexual men, hemophiliacs, Hatians, and intravenous drug abusers); however, individuals belonging to no apparent high-risk groups have also developed the disease. AIDS is generally spread by intimate sexual contact or by the administration of infected blood products, and occasionally by the maternal-fetal route. Many patients who develop AIDS are asymptomatic when they transmit their disease to contacts because a 6-month to 5-year (or more) latency interval may exist between infection and clinical manifestations of illness.

Although there is no effective therapy for AIDS, a number of compounds are currently under study as HTLV-III/LAV inhibitors, both in clinical trials and in model systems. Retroviral DNA polymerase (reverse transcriptase) plays a unique and essential role in the life cycle of HTLV-III/LAV, and this enzyme can be a target for antiviral therapy. Among the potential drugs being studied for use against AIDS which inhibit this enzyme are suramin and its analogs, ribavirin, foscarnet, and HPA-29. Biological response modifiers such as alpha and gamma interferon, interleukin-2, and monoclonal antibodies are also being evaluated. Comparative data for a number of these materials have recently been reviewed by B. J. Oberg in Antimicrob. Chemo. 1986, 17, 549–551. Although a number of anti-viral agents are currently being considered for experimental therapy of AIDS, to data no therapy has been shown to cure HTLV-III/LAV infection, or to completely restore the underlying immunodeficiency. Moreover, the chronicity of the infection, and the propensity of the virus to infect the brain, make it necessary to explore new classes of drugs that have the potential of oral administration and penetration across the blood-brain barrier.

Historically, nucleosides have been among the best antiviral drugs for treating DNA and RNA viral infections. Several known active agents of this class [e.g., 3-azido-3'-deoxythymidine (AZT), ribavirin] have been evaluated against HTLV-III/LAV in vitro, and AZT, a compound with activity in test systems, is currently in Phase I/II clinical trials. Other compounds which have been found to be effective in protecting cells against the cytopathic effects of HTLV-III/LAV in vitro are 2',3'-dideoxy (dd) analogs of physiologically important nucleosides.

These compounds, as their 5'-triphosphates, are known to terminate growing DNA chains because they lack the 3'-hydroxyl group required for further polymerization. This termination process forms the basis for the Sanger DNA sequencing method. While different cell types appear to vary significantly in their aibilities to phosphorylate 2',3'-dideoxynucleosides to the mono-, di-, and triphosphate levels, the corresponding end product triphosphates are known to strongly inhibit reverse transcriptase, as well as beta and gamma DNA polymerase. However, DNA polymerase alpha, the key synthetic enzyme for the DNA replication during cell growth, is much less affected.

While the 2',3'-dideoxy analogs of adenonsine (ddA), guanosine, inosine, thymidine, and cytidine (ddC) are all very effective in protecting T4+ lymphocytes against the cytopathic effects of HTLV-III/LAV in vitro, 2',3'-dideoxycytidine appears to be the most potent member of the group on the basis of molarity. At the non-cytotoxic concentrations of 0.5 and 5.0 micromoles, ddC provided essentially 100% protection to T4+ lymphocytes exposed to what would be an otherwise cytopathic dose of HTLV-III/LAV virus. However, some dideoxy nucleosides, e.g., ddA, are not very soluble in water or body fluids, and therefore is difficult to formulate for easy intravenous administration.

SUMMARY OF THE INVENTION

It is an object of the present invention to overcome deficiencies in the prior art, such as those indicated above.

It is anotherobject to provide for improved anti-viral therapy, both against RNA viruses and against DNA viruses.

It is still another object of the invention to provide compounds, including their phosphorylated derivatives, which are effective in the treatment of AIDS and other human or animal diseases caused by retroviruses.

It is a further object of the invention to provide compounds for the treatment of viral diseases which effectively inhibit the action of reverse transcriptase so that the viruses being affected cannot reproduce themselves in the host cells.

It has now been found that 5-substituted-2',3'-dideoxycytidine analogs and their phosphorylated derivatives are effective inhibitors of HTLV-III/LAV infection.

The compounds of the present invention have the following formulae and are identified by numbers 10, 15, 17, and 22.

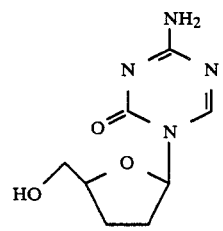

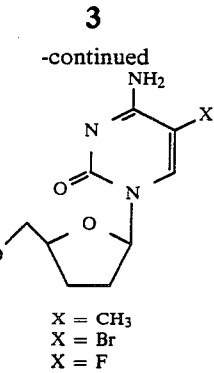

X = CH₃
X = Br
X = F the sensitivity of 2',3'-dideoxynucleoside analogs to acidic conditions. The reaction scheme is shown in Scheme I. The 5'-hydroxyl group of 4 was blocked with the dimethoxytrityl group to give 5, and a reductive procedure was followed to remove one of the secondary hydroxyl groups. This involved the preparation of the cyclic thiocarbonate 6 with thiocarbonyldiimidazole followed by reduction with tri-n-butyltin hydride to give a mixture of 2',3'-deoxy derivatives, 7a and 7b. The second hydroxyl group was removed by repeating this procedure, and gave compound 9 via a mixture of monothiourethanes, 8a, 8b. The dimethoxytrityl group was removed by mild hydrolysis on silica gel to produce the target compound.

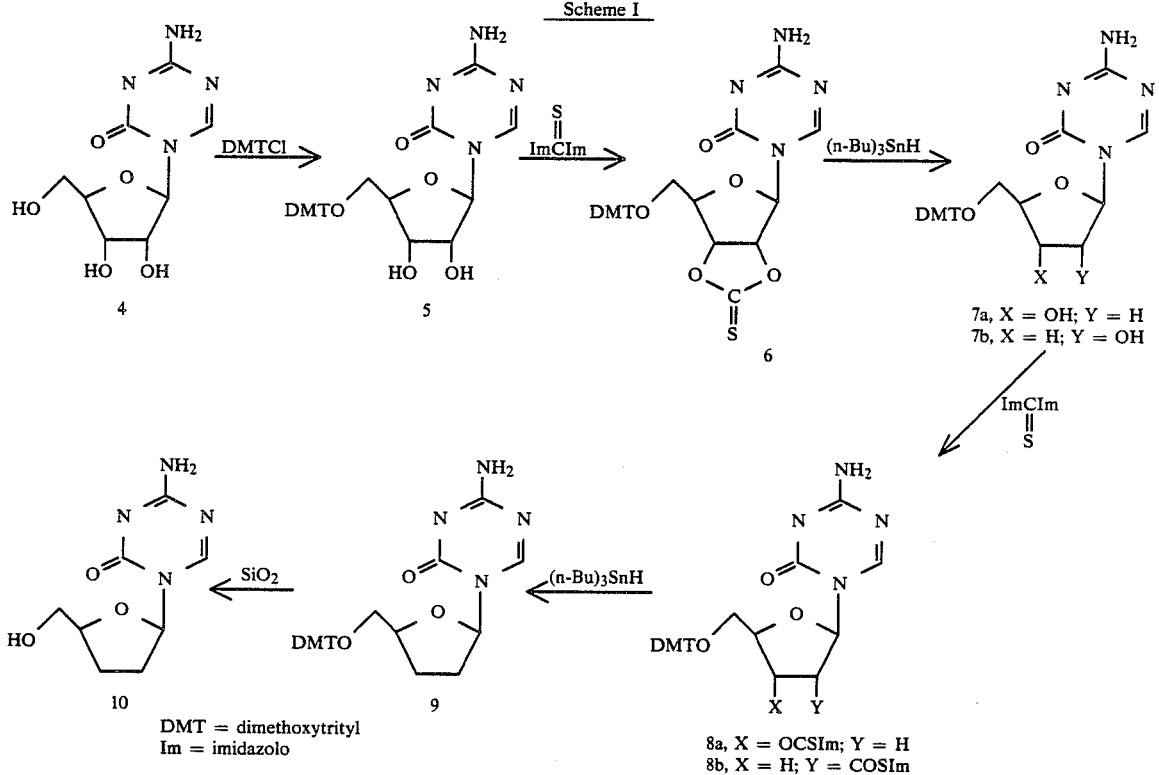

Scheme I

DMT = dimethoxytrityl
Im = imidazolo

The above 5-substituted-2',3-dideoxycytidine analogs were found to protect T4+ lymphocytes in vitro from the cytopathic effects of the HTLV-III/LAV virus, the causative agents of AIDS.

Although early reports had shown that 2',3'-dideoxycytidine (ddC) is a potent protective agent, this particular activity is abolished when this molecule is substituted at the 5-position. However, when the substitution is fluorine or aza, both activity and potency are retained.

The compounds can be phosphorylated at the 5' position to form nucleotides. Both the unphosphorylated and the phosphorylated compounds can be administered to an infected host, e.g., orally, intravenously, or the like.

DETAILED DESCRIPTION OF THE INVENTION

EXAMPLE I

The 2',3'-dideoxy-5-azacytidine analog 10 was prepared with caution, because of the known instability of 5-azacytidine analogs toward nucleophilic attack, and

EXAMPLE II

The 5-methyl analog, 15, was prepared from thymidine using the reductive sequence described above. 5-Tritylthymidine 11 was converted to the thiocarbonylimidazole derivative, 12, which was reduced to the dideoxy analog 13. A thymidine-cytidine conversion to produce 15 was accomplished by the method of Divakar and Reese in J. Chem. Soc. Perkin I 1982, 1171-1176, following ammonolysis of the intermediate 4-triazole derivative 14 and deprotection.

EXAMPLE III

The 5-bromo analog, 17, was prepared from 2',3'-dideoxycytidine 1 by bromination with N-bromosuccinimide using the general method of Srivastava and Nagpal, Experientia 1970, 26, 220.

EXAMPLE IV

The 5-fluoro analog 22 was prepared from the 5-O-trimethylacetyl (pivaloyl) analog 18 of 5-fluoro-2'-deoxyuridine. Using the Prisbe and Martin modification, Syn. Comm., 1985, 15, 401-409, of the above-described deoxygenation sequence, 19 was reduced to produce the dideoxy analog 20 which was converted to the 4-thio derivative 21 with Lawesson's reagent. Treatment of 21 with ammonia gave 22.

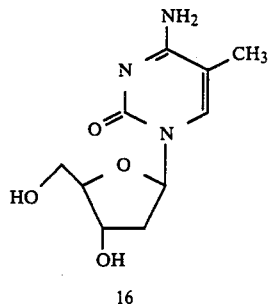

16

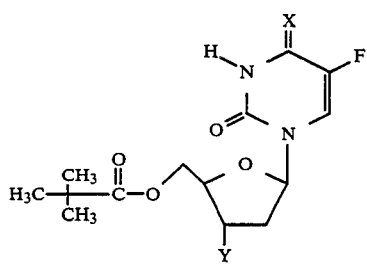

18, X = O; Y = OH
19, X = O; Y = OCSOCH₃
20, X = O; Y = H
21, X = S; Y = H

The 5-aza analog, Example I, has significant anti-HTLV-III activity at a 10 micromolar concentration, but was clearly more cytotoxic than ddC, as shown in Table I. This is consistent with the finding that the ribofuranosyl and 2'-deoxyribofuranosyl analogs of 5-azacytosine are both very cytotoxic antitumor agents. 5-Methyl-2',3'-dideoxycytidine was found to be devoid of protective effects, but began to show toxicity at 100 micromolar. By comparison, the nucleoside with only partial reduction of the sugar, 5-methyl-2'-deoxycytidine 16, is neither protective nor cytotoxic. This was also the case for the 5-bromo analog 17. Since bromine and methyl have similar steric volumes, but have opposite sigma values, these data imply that 5-position electronic effects do not play a dominant role in the activity of these compounds.

TABLE I

Protective Effect of 2',3'-Dideoxynucleosides Against HTLV-III/LAV Pathogenesis

| Compound | Conc. (μM) | Protective[a] Effect (%) | Cytotoxicity[b] (%) |
|---|---|---|---|
| (1) ddC | 0.05,0.5, 5,50 | 18,97, 100,77 | 0,0, 0,30 |
| (2) ddA | 1,5,10 50,100,200 | 42,98,100, 100,100,100 | 0,6,0, 0,0,0 |
| (3) ddT | 10,50,100, 200,500, 1000,2000 | 3,9,19, 77,68, 46,43 | 8,8,13, 6,30, 40,53 |
| (10) dd-5-AC | 1,10,50 | 16,58,38 | 13,19,62 |
| (15) 5-CH₃—ddC | 2,10,100 | 2,7,3 | 23,27,44 |
| (17) 5-Br—ddC | 1,10,30,200 | 6,8,5,0 | 14,14,2,0 |
| (22) 5-F—ddC | 0.05,0.5, 5,50 | 5,100, 100,88 | 5,0, 0,9 |
| (24) ddCMP | 0.5,2,10 | 13,9,74 | 0,7,0 |
| (25) ddAMP | 1,5,10, 50,100,200 | 25,91,100, 83,100,100 | 2,10,6, 4,0,5 |

TABLE I-continued

Protective Effect of 2',3'-Dideoxynucleosides Against HTLV-III/LAV Pathogenesis

| Compound | Conc. (μM) | Protective[a] Effect (%) | Cytotoxicity[b] (%) |
|---|---|---|---|
| (26) ddTMP | 10,50,200 | 7,18,15 | 9,9,10 |

[a]The percentage of protective effect of a nucleoside was determined by the following formula:
100 × [(number of viable cells exposed to HTLV-III and cultured in the presence of the nucleoside) − (number of viable cells exposed to HTLV-II I cultured in the absence of the nucleoside)]/[(number of viable cells cultured alone) − (number of viable cells exposed to HTLV-III in the absence of the nucleoside)].
[b]The percentage of cytotoxicity was determined by the following formula:
100 × [1 − (number of viable cells cultured in the presence of the nucleoside)/(number of viable cells cultured alone)].

It was found that 2',3'-dideoxy-5-fluorocytidine 22 is as protective of HTLV-III infected cells as the lead compound 1. Given the similar steric effects, but significantly different sigma values characteristic of 5-fluoro and 5-hydrogen substitution, once again, electronic effects do not appear to affect the activity of these compounds. However, if the activities of molecules with the sterically smaller groups 1, 10, 22 are compared with those containing the larger groups 15, 17, the indication is that large groups in the 5-position are detrimental to the anti-HTLV-III activity of 2',3'-dideoxycytidine analogs.

In order to be active against HTLV-III/LAV reverse transcriptase, the 2',3'-dideoxynucleosides must be converted to their 5'triphosphates. The rate at which these nucleotides are formed appears to vary with the type of cells treated. The first step in this metabolic process, the formation of the monophosphate, is critical, since a high nucleoside $K_m$ value for the appropriate deoxynucleoside kinase can result in poor reverse transcriptase inhibitory activity. Additionally, reduced kinase activity can be a cause for the development of resistance as is the case with nucleoside antitumor agents. While it is generally thought that nucleotides do not readily penetrate cell membranes because of their ionic character and relatively low lipophilicity, the nucleoside monophosphates, if effective, would be obviously superior to unphosphorylated drugs. In 1975, Plunkett and Cohen reported, in Cancer Research, 1975, 35, 1547-1554, that 2',3'-dideoxyadenosine-5'-phosphate appeared to enter mouse fibroblasts intact, with cytotoxic consequences.

The activities of the 5'-monophosphates of the dideoxy analogs of cytidine 24, adenosine 25, and thymidine 26 were compared, as shown in Table I.

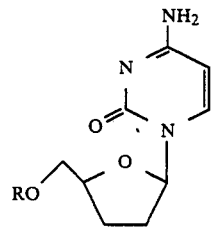

1, R = H
24, R = PO₃(NH₄)₂

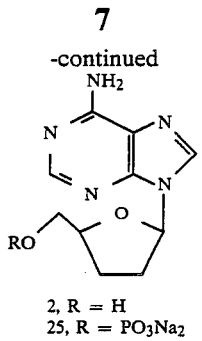

2, R = H
25, R = PO$_3$Na$_2$

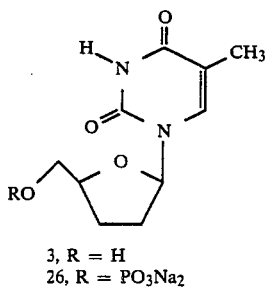

3, R = H
26, R = PO$_3$Na$_2$

Thymidine monophosphate 26 is the best candidate to test this approach because of the unusually high doses of dideoxythymidine 3 required for the protection of HTLV-III/LAV infected cells relative to the other dideoxy nucleosides. The high doses of dideoxythymidine required for protection probably relate to the very slow rate of phosphorylation for this compound. If preformed metabolite, i.e., thymidine 26, were able to penetrate the cell membrane, triphosphate formation might be facilitated, resulting in a lowered effective dose. This did not occur, as shown in Table I, and thymidine was found to be essentially inactive and noncytotoxic at 200 micromolar, a concentration which afforded considerable protection with the nucleoside dideoxythymidine 3. This was also the case with ddCMP 24, although significant protection was beginning to be observed at doses approximately ten times higher than were required for activity with ddC 1. The results with ddAMP 25 were different in that the nucleotide appeared to be just as active as the nucleoside 2, over a wide concentration range, However, ddAMP was not more potent at low concentrations, leading to the suspicion that conversion of ddAMP to ddA might be occurring though the action of a phosphatase. Nevertheless, it is possible that ddAMP might be penetrating the cell intact. In addition, 25 might offer some practical advantage over the relatively insoluble ddA in a clinical formulation.

The parent compound, 2',3'-dideoxycytidine, has been found to enter the central nervous system, very poorly. However, the 2',3'-dideoxy-5-fluorocytidine has been found to penetrate the blood-brain barrier because it is less basic than the parent compound, and is less protonated than the parent compound. Any substituent on 1 that makes the compound more lipophilic may make the compound more susceptible to penetration of the blood-brain barrier and therefore effective against the AIDS virus in the brain.

EXPERIMENTAL

Biological

HTLV-III/LAV cytopathic effect assay was performed using ATH8 cells as previously described.*

Briefly, 2×10$^5$ ATH8 cells were exposed to HTLV-III$_B$ virus (2,000 virus particles/cell) for 45 min after treatment with polybrene, resuspended in 2 ml of culture medium containing interleukin 2 in the presence or absence of various concentrations of compounds, and incubated in culture tubes at 37° C. in 5% CO$_2$/95% air humidifedd atmosphere. Control cells were treated similarly but were not exposed to the virus. At various time points on days 5 to 7 of culture, the total viable cells were counted in a hemocytometer by the trypan blue dye exclusion method.

*Proc. Nat. Acad. Sci. USA 1986, 83, 1911-1915.

Chemical

Commercially available synthetic reagents were purchased from the Aldrich Chemical Co. 5-Azacytidine, 2'-deoxy-5-fluorouridine and 2',3'-dideoxycytidine were obtained from the Drug Synthesis and Chemistry Branch, Developmental Therapeutics Program, NCI. 5-Methyl-2'-deoxycytidine (16) was purchased from Sigma Chemical Co. The dideoxynucleosides (1–3) and their monophosphates (24–26) were obtained from Pharmacia P-L Biochemicals. Preparative TLC plates were Taper Plates from the Analtech Corp. Thomas-Hoover melting points were uncorrected. Elemental analyses were carried out by Galbraith Laboratories, Knoxville, TN. $^1$H NMR data were obtained on a Varian XL-200 instrument. Positive ion fast atom bombardment (FAB) mass spectra were acquired with a VG Analytical 7070E mass spectrometer operated under the control of a VG 2035 data system.

5'-O-(4,4'-Dimethoxytrityl)-5-azacytidine (5)

To a solution of 5-azacytidine (2.20 g, 9 mmol) in dry pyridine (45 mL) was added 4,4'-dimethoxytrityl chloride (3.15 g, 9.3 mmol) and the mixture was stirred overnight. The reaction mixture was poured into ice-water and extracted with chloroform. The combined organic extracts were dried (MgSO$_4$) and chromatographed through a silica gel column (ethyl acetate—10% methanol/ethyl acetate) to give 2.89 g (59%) of a white product. NMR (CDCl$_3$+D$_2$O); δ 3.35 (m, 2H), 3.70 (s, 6H), 4.26 (m, 3H), 5.80 (d, 1H), 6.80 (m, 4H), 7.31 (m, 9H), 8.45 (s, 1H).

5'-O-(4,4'-dimethoxytrityl)-5-azacytidine-2',3'-O-cyclic thiocarbonate (6)

To a solution of compound 5 (0.55 g, 1 mmol) in anhydrous acetonitrile (25 mL) was added 1,1'-thiocarbonyldiimidazole (0.45 g, 2.27 mmol) and the mixture was stirred under nitrogen overnight. Solvent was evaporated and the residue was chromatographed through a silica gel column (ethyl acetate) to give 0.53 g (90%) of a white foam. NMR (D$_2$O); δ 3.49 (m, 2H), 3.80 (s, 6H), 4.42 (m, 2H), 4.63 (m, 1H), 5.78 (d, 1H), 6.80 (m, 4H), 7.31 (m, 9H), 7.98 (s, 1H).

Anal. C$_{30}$H$_{28}$N$_4$O$_7$S; C, H, N, S (ΔC=−0.54)

Mixture of 5'-O-(4,4'-dimethoxytrityl) derivatives of 2'-deoxy (7a) and 3'-deoxy-5-azacytidine (7b)

To a solution of compound 6 (0.53 g, 0.90 mmol) in anhydrous toluene (25 mL) was added α,α'-azaisobutyronitrile (AIBN) (0.02 g, 0.12 mmol) and tri-n-butyltin hydride (1.7 mL, 6.52 mmol). The mixture was heated to 110°–120° C. for 2 h, solvent was evaporated, and the residue was purified on preparative TLC (5% methanol/ethyl acetate) to give 0.19 g (41%) of mixture of 7a and 7b which was used without further purification.

2',3'-Dideoxy-5'-O-(4,4'-dimethoxytrityl)-5-azacytidine (9)

To a solution of the mixture of 7a and 7b (0.38 g, 0.72 mmol) in anhydrous acetonitrile (10 mL) was added 1,1'-thiocarbonyldiimidazole (0.3 g, 1.87 mmol) and the mixture was stirred under nitrogen for 24 h. Solvent was evaporated and the residue was chromatographed through a silica gel column (ethyl acetate→10% methanol/ethyl acetate) to give 0.32 g (71%) of a mixture of 8a and 8b. This mixture was dissolved in anhydrous toluene (20 mL), AIBN (0.02 g, 0.12 mmol) and tri-n-butyltin hydride (1.9 mL, 7.28 mmol) were added, and the mixture was heated to 110°-120° C. for 2 h. Solvent was evaporated and the residue was purified by preparative TLC (10% methanol/ethyl acetate) to give 0.12 g (47%) of white foam. NMR (CDCl$_3$+D$_2$O); δ 2.20 (m, 4H), 3.37 (m, 2H), 3.80 (s, 6H), 4.23 (m, 1H), 5.97 (d, 1H, J=5 Hz), 6.80 (m, 4H), 7.31 (m, 9H), 8.5 (s, 1H).

2',3'-Dideoxy-5-azacytidine (10)

Compound 9 (0.08 g, 0.16 mmol) was dissolved in chloroform (2 mL) and poured onto a silica gel column (3 g, Whatman Partisil 40). The column was washed with benzene (40 mL) and left at ambient temperature for 24 h. The column was eluted with ethyl acetate followed by 10% methanol/ethyl acetate to give 0.02 g of crude product along with 0.04 g of unchanged starting material. The crude product was dissolved in water, filtered through a Millex-GS Filter, and the filtrate was chromatographed through a C$_{18}$ reverse-phase column (10% methanol/water) to give 0.005 g (30%) of white, lyophilized product. NMR (D$_2$O); δ 2.06 (m, 4H), 3.72 (m, 2H), 4.18 (m, 1H), 5.89 (d, 2H, J=5 Hz), 8.51 (s, 1H). FAB mass spectrum, m/z (relative intensity) 113 (b+2H, 100), 213 (MH$^+$, 88). MH$^+$ calc. 213.0988; found 213.0991±0.0020 (n=8).

5'-O-Tritylthymidine (11)

This compound was prepared from thymidine and triphenylmethyl chloride in dry pyridine by the procedure of Horwitz and Urbanski.
*J. Org. Chem. 1962, 27, 3300-3302.

2'-O-(1-Imidazolyl)thiocarbonyl-5'-O-tritylthymidine (12)

To a solution of 11 (0.49 g, 1 mmol) in dry acetonitrile (15 mL) was added 0.42 g (2.1 mmol) of 1,1'-thiocarbonyldiimidazole and the solution was heated to 90° C. for 3 h under nitrogen. The reaction mixture was cooled, the solvent evaporated, and the residue chromatographed on a preparative TLC plate (ethyl acetate) to give 0.43 g (72%) of a white foam. NMR (CDCl$_3$); δ 1.45 (s, 3H), 2.71 (m, 3H), 3.57 (m, 2H), 4.34 (m, 1H), 6.14 (m, 1H), 6.45 (br s, 1H), 7.29 (m, 15H), 7.61 (s, 1H), 7.65 (s, 1H), 8.09 (s, 1H), 8.66 (s, 1H).

2'-Deoxy-5'-O-tritylthymidine (13)

To a solution of compound 12 (0.35 g, 0.58 mmol) in dry toluene (20 mL) was added AIBN (0.05 g, 0.29 mmol) and tri-n-butyltin hydride (3.1 mL, 11.5 mmol), and the mixture was heated to 120° C. for 1 h. The reaction mixture was cooled, solvent was evaporated, and the residue was chromatographed on a preparative TLC plate (1:1 ethyl acetate/hexane) to give 0.15 g (55%) of a white foam. NMR (CDCl$_3$+D$_2$O); δ 2.06 (s, 3H), 2.14 (m, 3H), 2.45 (m, 1H), 3.42 (m, 2H), 4.12 (m, 1H), 6.14 (m, 1H), 7.20 (m, 15H), 7.62 (s, 1H).

2',3'-Dideoxy-5'-O-tritylribosyl-5-methyl-4-[1-(1,2,4-triazolyl)]-pyrimidin-2-one (14)

Triethylamine (8.9 mL, 64 mmol) was added to a stirred, 0° C. mixture of 1,2,4-triazole (4.61 g, 66.92 mmol), phosphoryl chloride (1.34 mL, 14.89 mmol) and acetonitrile (20 mL). To the resulting mixture was added a solution of compound 13 (1.16 g, 2.47 mmol) in acetonitrile (10 mL) and the reaction mixture was stirred under ambient conditions for 1.5 h. After the solvent was evaporated, the residue was dissolved in chloroform. This solution was washed with saturated sodium bicarbonate solution, and dried (MgSO$_4$). Solvent was evaporated and the residue was chromatographed on a preparative TLC plate (ethyl acetate) to give 0.69 g (54%) of white product. NMR (CDCl$_3$); δ 2.0 (s, 3H), 2.1 (m, 3H), 2.4 (m, 1H), 3.4 (m, 2H), 4.2 (m, 1H), 6.1 (m, 1H), 7.2 (m, 16H), 8.0 (s, 1H), 8.2 (s, 1H).

2',3'-Dideoxy-5-methylcytidine (15)

To a solution of compound 14 (0.52 g, 1 mmol) in dioxane (10 mL) was added 2 mL of concentrated ammonium hydroxide and the solution was stirred for 5 h. After the solvents were evaporated, the residue was again dissolved in dioxane (10 mL) and the solution was stirred with 5 mL of AG 50W-X8 resin overnight. The resin mixture was placed in a column and washed with 50% aqueous methanol followed by 2N NH$_4$OH. The ammonium hydroxide eluent was lyophilized to give a crude product which was further purified through a C$_{18}$ reverse phase column (15% CH$_3$OH/water) to give 0.11 g (48%) of a lyophilized white solid. NMR (D$_2$O); δ 1.8 (m, 1H), 2.0 (s, 3H), 2.1 (m, 2H), 2.45 (m, 1H), 6.14 (m, 1H), 7.78 (s, 1H). FAB mass spectrum; m/z (relative intensity) 101 (sugar, 14), 126 (b+2H, 100), 226 (MH$^+$, 19). Anal. C$_{10}$H$_{15}$N$_3$O$_3$.0.7H$_2$O; C, H, N. (ΔH=−0.49).

2',3'-Dideoxy-5-bromocytidine (17) To a solution of 2',3'-dideoxycytidine (0.127 g, 0.6 mmol) in dry DMF (1.5 mL) was added N-bromosuccinimide (0.117 g, 0.65 mmol) and the mixture was stirred under nitrogen overnight. Solvent was removed in vacuo and the residue was chromatographed on a preparative TLC plate (ethyl acetate/methanol/triethylamine=90/10/1) to give 0.097 g (57%) of white solid, mp 188°-190° C. (dec) after recrystallization from acetone-hexane. NMR (D$_2$O); δ 1.94 (m, 2H), 2.02 (m, 1H), 2.45 (m, 1H), 3.74 (dd, 1H), 4.01 (dd, 1H), 4.23 (m, 1H), 6.01 (dd, 1H), 8.70 (s, 1H). FAB mass spectrum; m/z (relative intensity) 112 (b+3H−Br, 99), 190 ([$^{79}$Br]b+2H, 68), 192 ([$^{81}$Br]b+2H, 70), 212 (M+2H−Br, 100), 290 ([$^{79}$Br]MH+, 35), 292 ([$^{81}$Br]MH+, 35). Anal. C$_9$H$_{12}$N$_3$BrO$_3$; C, H, N, Br.

1-(2'-Deoxy-5'-O-trimethylacetyl-β-D-ribofuranosyl)-5-fluorouracil (18)

To a solution of 2'-deoxy-5-fluorouridine (1.23 g, 5 mmol) in anhydrous pyridine (10 mL) was added trimethylacetyl (pivaloyl) chloride (0.7 mL, 5.6 mmol) and the mixture was stirred overnight. Pyridine and the excess trimethylacetyl chloride were removed in vacuo and the residue was dissolved in cold water. After extraction with chloroform, the combined organic extracts were dried (MgSO$_4$), solvent removed in vacuo and the residue was chromatographed through a silica gel column (Kiesel gel 60, 1:1 ethyl acetate/hexane) to give 1.16 g (70%) of product. Recrystallization from ethyl acetate/hexane gave white needles, mp 135.5°–136.5° C. NMR (CDCl$_3$); δ 1.23 (s, 9H), 2.04 (m, 1H), 2.57 (m, 2H), 4.27 (m, 1H), 4.42 (m, 2H), 6.25 (m, 1H), 7.62 (d, J=6 Hz, 1H), 9.7 (br s, 1H).

2′-Deoxy-3′-methoxythiocarbonyloxy-5′-trimethylacetyl-5-fluorouridine (19)

To a solution of compound 18 (0.66 g, 2 mmol) in anhydrous acetonitrile (30 mL) was added 1,1′-thiocarbonyldiimidazole (0.80 g, 4 mmol) and the mixture was heated at 90° C. under nitrogen overnight. Solvent was evaporated, anhydrous methanol (10 mL) was added, and the resulting mixture heated to 60°–65° C. for 2 h. Solvent was evaporated and the residue was chromatographed through a silica gel column (Kiesel gel 60, ethyl acetate/hexane=7/3) to give 0.54 g (67%) of white product, mp, 128°–128.5° after recrystallization from acetone-hexane. NMR (CDCl$_3$); δ 1.24 (s, 9H), 1.56 (m, 1H), 2.05 (m, 1H), 2.63 (m, 1H), 4.08 (s, 3H), 4.35 (m, 1H), 4.52 (m, 2H), 6.28 (m, 1H), 7.61 (d, J=6 Hz, 1H), 8.61 (br s, 1H). Anal C$_{16}$H$_{21}$N$_2$O$_7$FS; C, H, N, S, F.

2′,3′-Dideoxy-5′-O-trimethylacetyl-5-fluorouridine (20)

To a solution of compound 19 (0.40 g, 1 mmol) in dry toluene (20 mL) was added AIBN (0.08 g, 0.5 mmol) and tri-n-butyltin hydride (5.4 ml, 20 mmol). The mixture was heated at 120°–125° C. for 0.5 h. Solvent was removed and the residue purified on a preparative TLC plate (1:1 ethyl acetate/hexane) to give 0.21 g (68%) of a white foam. NMR (CDCl$_3$); δ 1.16 (s, 9H), 1.78 (m, 1H), 1.98 (m, 2H), 2.42 (m, 1H), 4.26 (m, 3H), 5.96 (m, 1H), 7.64 (d, J=6 Hz, 1H), 9.87 (br s, 1H). Anal C$_{14}$H$_{19}$N$_2$O$_5$F.0.5H$_2$O; C, H, N, F.

2′,3′-Dideoxy-5′-O-trimethylacetyl-4-thio-5-fluorouridine (21)

To a solution of compound 20 (0.41 g, 1.30 mmol) in anhydrous benzene (30 mL) was added 1.15 g (2.8 mmol) of Lawesson's reagent and the mixture was heated to 110° C. for 2 h. The reaction mixture was cooled and filtered through a bed of Celite. Solvent was evaporated and the residue was chromatographed through a silica gel column (Kiesel gel 60, 1:1 ethyl acetate/hexane) to give 0.27 g (62%) of a greenish foam which was used without further purification.

2′,3′-Dideoxy-5-fluorocytidine (22)

To a solution of compound 21 (0.1 g, 0.3 mmol) in chloroform (2 mL) was added 50 mL of saturated methanolic ammonia and the mixture was heated in a stainless steel bomb at 120° C. (ca. 90 psi) for 24 h. Upon cooling, the solvent was evaporated and the residue was eluted through a C$_{18}$ reverse-phase column (10% CH$_3$OH/H$_2$O) to give 0.35 g (70%) of a white lyophilized product. NMR (D$_2$O); δ 1.78 (m, 1H), 2.06 (m, 2H), 2.44 (m, 1H), 3.82 (m, 2H), 4.22 (m, 1H), 6.02 (m, 1H), 8.06 (d, J=6 Hz, 1H); FAB mass spectrum; m/z (relative intensity) 130 (b+2H, 100), 230 (MH+, 76). Anal. C$_9$H$_{12}$N$_3$O$_3$F.0.75H$_2$O; C, H, N.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A 5-substituted 2′,3′-dideoxycytidine compound of the formula:

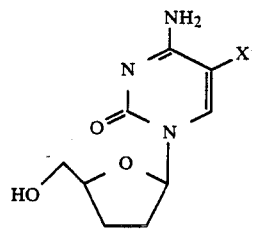

wherein X is selected from the group consisting of bromine and fluorine.

2. The compound according to claim 1 wherein X is fluorine.

3. The compound according to claim 1 wherein X is bromine.

4. A phosphorylated compound of the formula

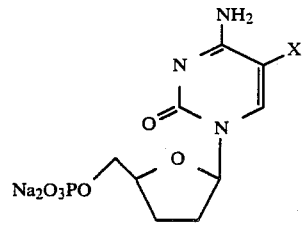

wherein X is selected from the group consisting of bromine and fluorine.

5. The compound of claim 4 wherein X is bromine.

6. The compound according to claim 4 wherein X is fluorine.

7. A method for protecting cells against HIV pathogenesis comprising treating said cells with an effective amount of a compound according to claim 1.

8. A method for protecting cells against HIV pathogenesis comprising treating said cells with an effective amount of a compound according to claim 4.

* * * * *